(12) United States Patent
Bruinsma et al.

(10) Patent No.: US 9,186,102 B2
(45) Date of Patent: *Nov. 17, 2015

(54) EMITTER DRIVER FOR NONINVASIVE PATIENT MONITOR

(71) Applicant: CERCACOR LABORATORIES, INC., Irvine, CA (US)

(72) Inventors: Johannes Bruinsma, Opeinde (NL); Cristiano Dalvi, Lake Forest, CA (US); Marcelo Lamego, Cupertino, CA (US)

(73) Assignee: CERCACOR LABORATORIES, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/227,230

(22) Filed: Mar. 27, 2014

(65) Prior Publication Data

US 2014/0296664 A1 Oct. 2, 2014

Related U.S. Application Data

(63) Continuation of application No. 12/875,062, filed on Sep. 2, 2010, now Pat. No. 8,688,183.

(60) Provisional application No. 61/239,741, filed on Sep. 3, 2009.

(51) Int. Cl.
*A61B 5/00* (2006.01)
*A61B 5/1455* (2006.01)

(52) U.S. Cl.
CPC ........... *A61B 5/14552* (2013.01); *A61B 5/0059* (2013.01); *A61B 5/6826* (2013.01); *A61B 2560/045* (2013.01); *A61B 2562/0233* (2013.01); *A61B 2562/046* (2013.01); *A61B 2562/222* (2013.01)

(58) Field of Classification Search
USPC .......................... 600/310, 322–324, 336, 473
See application file for complete search history.

(56) References Cited

U.S. PATENT DOCUMENTS

| 4,114,604 A | 9/1978 | Shaw et al. |
| 4,258,719 A | 3/1981 | Lewyn |
| 4,267,844 A | 5/1981 | Yamanishi |
| 4,444,471 A | 4/1984 | Ford et al. |

(Continued)

FOREIGN PATENT DOCUMENTS

| EP | 419223 | 3/1991 |
| WO | WO93/12712 | 7/1993 |

(Continued)

OTHER PUBLICATIONS

European Office Action issued in application No. 10763901.5 on Aug. 27, 2014.

(Continued)

*Primary Examiner* — Minh Phan
(74) *Attorney, Agent, or Firm* — Knobbe, Martens, Olson & Bear LLP

(57) ABSTRACT

Embodiments of the present disclosure include an emitter driver configured to be capable of addressing substantially $2^N$ nodes with N cable conductors configured to carry activation instructions from a processor. In an embodiment, an address controller outputs an activation instruction to a latch decoder configured to supply switch controls to activate particular LEDs of a light source.

20 Claims, 10 Drawing Sheets

(56) References Cited

U.S. PATENT DOCUMENTS

| | | |
|---|---|---|
| 4,655,225 A | 4/1987 | Dahne et al. |
| 4,684,245 A | 8/1987 | Goldring |
| 4,755,676 A | 7/1988 | Gaalema et al. |
| 4,781,195 A | 11/1988 | Martin |
| 4,805,623 A | 2/1989 | Jöbsis |
| 4,880,304 A | 11/1989 | Jaeb et al. |
| 4,960,128 A | 10/1990 | Gordon et al. |
| 4,964,408 A | 10/1990 | Hink et al. |
| 5,028,787 A | 7/1991 | Rosenthal et al. |
| 5,035,243 A | 7/1991 | Muz |
| 5,041,187 A | 8/1991 | Hink et al. |
| 5,043,820 A | 8/1991 | Wyles et al. |
| 5,069,213 A | 12/1991 | Polczynski |
| 5,069,214 A | 12/1991 | Samaras et al. |
| 5,077,476 A | 12/1991 | Rosenthal |
| D326,715 S | 6/1992 | Schmidt |
| 5,122,925 A | 6/1992 | Inpyn |
| 5,131,391 A | 7/1992 | Sakai et al. |
| 5,137,023 A | 8/1992 | Mendelson et al. |
| 5,159,929 A | 11/1992 | McMillen et al. |
| 5,163,438 A | 11/1992 | Gordon et al. |
| 5,222,295 A | 6/1993 | Dprris, Jr. |
| 5,222,495 A | 6/1993 | Clarke et al. |
| 5,222,496 A | 6/1993 | Clarke et al. |
| 5,249,576 A | 10/1993 | Goldberger et al. |
| 5,278,627 A | 1/1994 | Aoyagi et al. |
| 5,297,548 A | 3/1994 | Pologe |
| 5,319,355 A | 6/1994 | Russek |
| 5,337,744 A | 8/1994 | Branigan |
| 5,337,745 A | 8/1994 | Benaron |
| 5,341,805 A | 8/1994 | Stavridi et al. |
| 5,362,966 A | 11/1994 | Rosenthal et al. |
| D353,195 S | 12/1994 | Savage et al. |
| D353,196 S | 12/1994 | Savage et al. |
| 5,377,676 A | 1/1995 | Vari et al. |
| D356,870 S | 3/1995 | Ivers et al. |
| D359,546 S | 6/1995 | Savage et al. |
| 5,427,093 A | 6/1995 | Ogawa et al. |
| 5,431,170 A | 7/1995 | Mathews |
| D361,840 S | 8/1995 | Savage et al. |
| 5,437,275 A | 8/1995 | Amundsen et al. |
| 5,441,054 A | 8/1995 | Tsuchiya |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,034 A | 1/1996 | Lewis et al. |
| 5,482,036 A | 1/1996 | Diab et al. |
| 5,490,505 A | 2/1996 | Diab et al. |
| 5,494,043 A | 2/1996 | O'Sullivan et al. |
| 5,511,546 A | 4/1996 | Hon |
| 5,533,511 A | 7/1996 | Kaspari et al. |
| 5,534,851 A | 7/1996 | Russek |
| 5,553,615 A | 9/1996 | Carim et al. |
| 5,553,616 A | 9/1996 | Ham et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| D378,414 S | 3/1997 | Allen et al. |
| 5,625,458 A | 4/1997 | Alfano et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,676,143 A | 10/1997 | Simonsen et al. |
| 5,685,299 A | 11/1997 | Diab et al. |
| D390,666 S | 2/1998 | Lagerlof |
| D393,830 S | 4/1998 | Tobler et al. |
| 5,743,262 A | 4/1998 | Lepper, Jr. et al. |
| 5,750,927 A | 5/1998 | Baltazar |
| 5,752,914 A | 5/1998 | Delonzor et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,792,052 A | 8/1998 | Isaacson et al. |
| 5,810,734 A | 9/1998 | Caro et al. |
| 5,823,950 A | 10/1998 | Diab et al. |
| 5,826,885 A | 10/1998 | Helgeland |
| 5,830,131 A | 11/1998 | Caro et al. |
| 5,833,618 A | 11/1998 | Caro et al. |
| D403,070 S | 12/1998 | Maeda et al. |
| 5,851,178 A | 12/1998 | Aronow |
| 5,860,919 A | 1/1999 | Kiani-Azarbayjany et al. |
| 5,890,929 A | 4/1999 | Mills et al. |
| 5,902,235 A | 5/1999 | Lewis et al. |
| 5,903,357 A | 5/1999 | Colak |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,957,840 A | 9/1999 | Terasawa et al. |
| D414,870 S | 10/1999 | Saltzstein et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,049,727 A | 4/2000 | Crothall |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,866 A | 11/2000 | Miesel et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,172,743 B1 | 1/2001 | Kley et al. |
| 6,181,958 B1 | 1/2001 | Steuer et al. |
| 6,184,521 B1 | 2/2001 | Coffin, IV et al. |
| 6,206,830 B1 | 3/2001 | Diab et al. |
| 6,223,063 B1 | 4/2001 | Chaiken et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,278,889 B1 | 8/2001 | Robinson |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| D452,012 S | 12/2001 | Phillips |
| 6,325,761 B1 | 12/2001 | Jay |
| 6,334,065 B1 | 12/2001 | Al-Ali et al. |
| 6,343,223 B1 | 1/2002 | Chin et al. |
| 6,343,224 B1 | 1/2002 | Parker |
| 6,345,194 B1 | 2/2002 | Nelson et al. |
| 6,349,228 B1 | 2/2002 | Kiani et al. |
| 6,353,750 B1 | 3/2002 | Kimura et al. |
| 6,360,113 B1 | 3/2002 | Dettling |
| 6,360,114 B1 | 3/2002 | Diab et al. |
| 6,360,115 B1 | 3/2002 | Greenwald et al. |
| D455,834 S | 4/2002 | Donars et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |

(56) References Cited

U.S. PATENT DOCUMENTS

| | | | |
|---|---|---|---|
| 6,430,437 B1 | 8/2002 | Marro | |
| 6,430,525 B1 | 8/2002 | Weber et al. | |
| D463,561 S | 9/2002 | Fukatsu et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,522,521 B2 | 2/2003 | Mizuno et al. | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,509 B2 | 8/2003 | Schmitt | |
| 6,606,511 B1 | 8/2003 | Ali et al. | |
| D481,459 S | 10/2003 | Nahm | |
| 6,632,181 B2 | 10/2003 | Flaherty et al. | |
| 6,636,759 B2 | 10/2003 | Robinson | |
| 6,639,668 B1 | 10/2003 | Trepagnier | |
| 6,639,867 B2* | 10/2003 | Shim | 365/230.06 |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,668,185 B2 | 12/2003 | Toida | |
| 6,671,531 B2 | 12/2003 | Al-Ali et al. | |
| 6,678,543 B2 | 1/2004 | Diab et al. | |
| 6,681,133 B2 | 1/2004 | Chaiken et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,010 B2 | 11/2004 | Seetharaman et al. | |
| 6,816,241 B2 | 11/2004 | Grubisic | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| D502,655 S | 3/2005 | Huang | |
| 6,861,639 B2 | 3/2005 | Al-Ali | |
| 6,898,452 B2 | 5/2005 | Al-Ali et al. | |
| 6,912,413 B2 | 6/2005 | Rantala et al. | |
| 6,920,345 B2 | 7/2005 | Al-Ali et al. | |
| D508,862 S | 8/2005 | Behar et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| D510,625 S | 10/2005 | Widener et al. | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| D514,461 S | 2/2006 | Harju | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,047,054 B2 | 5/2006 | Benni | |
| 7,067,893 B2 | 6/2006 | Mills et al. | |
| 7,092,757 B2 | 8/2006 | Larson et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| D535,031 S | 1/2007 | Barrett et al. | |
| D537,164 S | 2/2007 | Shigemori et al. | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,230,227 B2 | 6/2007 | Wilcken et al. | |
| D547,454 S | 7/2007 | Hsieh | |
| 7,239,905 B2 | 7/2007 | Kiani-Azarbayjany et al. | |
| 7,245,953 B1 | 7/2007 | Parker | |
| D549,830 S | 8/2007 | Behar et al. | |
| 7,254,429 B2 | 8/2007 | Schurman et al. | |
| 7,254,431 B2 | 8/2007 | Al-Ali | |
| 7,254,433 B2 | 8/2007 | Diab et al. | |
| 7,254,434 B2 | 8/2007 | Schulz et al. | |
| D550,364 S | 9/2007 | Glover et al. | |
| D551,350 S | 9/2007 | Lorimer et al. | |
| 7,272,425 B2 | 9/2007 | Al-Ali | |
| 7,274,955 B2 | 9/2007 | Kiani et al. | |
| D553,248 S | 10/2007 | Nguyen | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,295,866 B2 | 11/2007 | Al-Ali | |
| D562,985 S | 2/2008 | Brefka et al. | |
| 7,328,053 B1 | 2/2008 | Diab et al. | |
| 7,332,784 B2 | 2/2008 | Mills et al. | |
| 7,340,287 B2 | 3/2008 | Mason et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| D567,125 S | 4/2008 | Okabe et al. | |
| 7,355,512 B1 | 4/2008 | Al-Ali | |
| 7,356,365 B2 | 4/2008 | Schurman | |
| 7,365,923 B2 | 4/2008 | Hargis et al. | |
| D569,001 S | 5/2008 | Omaki | |
| D569,521 S | 5/2008 | Omaki | |
| 7,371,981 B2 | 5/2008 | Abdul-Hafiz | |
| 7,373,193 B2 | 5/2008 | Al-Ali et al. | |
| 7,373,194 B2 | 5/2008 | Weber et al. | |
| 7,376,453 B1 | 5/2008 | Diab et al. | |
| 7,377,794 B2 | 5/2008 | Al-Ali et al. | |
| 7,377,899 B2 | 5/2008 | Weber et al. | |
| 7,383,070 B2 | 6/2008 | Diab et al. | |
| 7,395,189 B2 | 7/2008 | Qing et al. | |
| 7,415,297 B2 | 8/2008 | Al-Ali et al. | |
| 7,428,432 B2 | 9/2008 | Ali et al. | |

(56) References Cited

U.S. PATENT DOCUMENTS

| | | |
|---|---|---|
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,153 B2 | 3/2009 | Blank et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,606,606 B2 | 10/2009 | Laakkonen |
| D603,966 S | 11/2009 | Jones et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,657,294 B2 | 2/2010 | Eghbal et al. |
| 7,657,295 B2 | 2/2010 | Coakley et al. |
| 7,657,296 B2 | 2/2010 | Raridan et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,809,418 B2 | 10/2010 | Xu |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,506 B2 | 3/2011 | Xu et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,044,998 B2 | 10/2011 | Heenan |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,126,531 B2 | 2/2012 | Crowley |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,219,170 B2 | 7/2012 | Hausmann et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,332,006 B2 | 12/2012 | Naganuma et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,380,272 B2 | 2/2013 | Barrett et al. |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,421,022 B2 | 4/2013 | Rozenfeld |
| 8,423,106 B2 | 4/2013 | Lamego et al. |
| 8,428,674 B2 | 4/2013 | Duffy et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |

(56) References Cited

U.S. PATENT DOCUMENTS

| | | |
|---|---|---|
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,503 B2 | 10/2013 | Vo et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,602,971 B2 | 12/2013 | Farr |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,909,310 B2 | 12/2014 | Lamego et al. |
| 2002/0016536 A1 | 2/2002 | Benni |
| 2002/0052547 A1 | 5/2002 | Toida |
| 2002/0091322 A1 | 7/2002 | Chaiken et al. |
| 2002/0115918 A1 | 8/2002 | Crowley |
| 2004/0039271 A1 | 2/2004 | Blank et al. |
| 2004/0039272 A1 | 2/2004 | Abdul-Hafiz et al. |
| 2004/0049237 A1 | 3/2004 | Larson et al. |
| 2004/0054269 A1 | 3/2004 | Rantala et al. |
| 2004/0054291 A1 | 3/2004 | Schulz et al. |
| 2004/0061120 A1 | 4/2004 | Mizuyoshi |
| 2004/0119542 A1 | 6/2004 | Seetharaman et al. |
| 2005/0162761 A1 | 7/2005 | Hargis et al. |
| 2006/0005944 A1 | 1/2006 | Wang et al. |
| 2006/0076473 A1 | 4/2006 | Wilcken et al. |
| 2006/0167347 A1 | 7/2006 | Xu et al. |
| 2006/0189859 A1 | 8/2006 | Kiani et al. |
| 2006/0208191 A1 | 9/2006 | Kessler et al. |
| 2006/0211924 A1 | 9/2006 | Dalke et al. |
| 2006/0220881 A1 | 10/2006 | Al-Ali et al. |
| 2006/0258922 A1 | 11/2006 | Mason et al. |
| 2007/0149865 A1 | 6/2007 | Laakkonen |
| 2007/0165218 A1 | 7/2007 | Qing et al. |
| 2007/0197886 A1 | 8/2007 | Naganuma et al. |
| 2007/0293792 A1 | 12/2007 | Sliwa et al. |
| 2008/0036855 A1 | 2/2008 | Heenan |
| 2008/0071154 A1 | 3/2008 | Hausmann et al. |
| 2008/0130232 A1 | 6/2008 | Yamamoto |
| 2008/0139908 A1 | 6/2008 | Kurth |
| 2008/0208006 A1 | 8/2008 | Farr |
| 2009/0030327 A1 | 1/2009 | Chance |
| 2009/0043180 A1 | 2/2009 | Tschautscher et al. |
| 2009/0105565 A1 | 4/2009 | Xu |
| 2009/0129102 A1 | 5/2009 | Xiao et al. |
| 2009/0163775 A1 | 6/2009 | Barrett et al. |
| 2009/0259114 A1 | 10/2009 | Johnson et al. |
| 2010/0004518 A1 | 1/2010 | Vo et al. |
| 2010/0030040 A1 | 2/2010 | Poeze et al. |
| 2010/0049018 A1 | 2/2010 | Duffy et al. |
| 2010/0090118 A1 | 4/2010 | Rozenfeld |
| 2011/0004082 A1 | 1/2011 | Poeze et al. |
| 2011/0105865 A1 | 5/2011 | Yu et al. |
| 2013/0317370 A1 | 11/2013 | Dalvi et al. |
| 2014/0066783 A1 | 3/2014 | Kiani et al. |
| 2014/0155712 A1 | 6/2014 | Lamego et al. |

FOREIGN PATENT DOCUMENTS

| | | |
|---|---|---|
| WO | WO 00/25112 | 5/2000 |
| WO | WO 2014/149781 | 9/2014 |
| WO | WO 2014/158820 | 10/2014 |

OTHER PUBLICATIONS

PCT International Search Report, App. No. PCT/US2010/047899, Date of Actual Completion of Search: Jan. 26, 2011, 4 pages.

International Search Report issued in Application No. PCT/US2009/052756, mailed Feb. 10, 2009 in 14 pages.

International Preliminary Report on Patentability and Written Opinion of the International Searching Authority issued in Application No. PCT/US2009/052756, mailed Feb. 8, 2011 in 8 pages.

International Search Report and Written Opinion for PCT/US2009/049638, mailed Jan. 7, 2010.

International Preliminary Report on Patentability and Written Opinion of the International Searching Authority issued in Application No. PCT US2009/049638, mailed Jan. 5, 2011 in 9 pages.

Burritt, Mary F.; Current Analytical Approaches to Measuring Blood Analytes; vol. 36; No. 8(B); 1990.

Kuenstner, et al., J. Todd; Measurement of Hemoglobin in Unlysed Blood by Near-Infrared Spectroscopy; vol. 48; No. 4, 1994.

Manzke, et al., B., Multi Wavelength Pulse Oximetry in the Measurement of Hemoglobin Fractions; vol. 2676; 1996.

Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.

Schmitt, Joseph M.; Simple Photon Diffusion Anaylsis of the Effects of Multiple Scattering on Pulse Oximetry; Mar. 14, 1991; revised Aug. 30, 1991.

Schmitt, et al., Joseph M.; Measurement of Blood Hematocrit by Dual-Wavelength near-IR Photoplethysmography; vol. 1641; 1992.

Schnapp, et al., L.M.; Pulse Oximetry. Uses and Abuses.; Chest 1990; 98; 1244-1250 DOI 10.1378/Chest.98.5.1244.

http://www.masimo.com/rainbow/pronto.htm Noninvasive & Immediate Hemoglobin Testing, printed on Aug. 20, 2009.

http://www.masimo.com/pulseOximeter/Rad5.htm; Signal Extraction Pulse Oximeter, printed on Aug. 20, 2009.

http://blogderoliveira.blogspot.com/2008_02_01_archive.html; Ricardo Oliveira, printed on Aug. 20, 2009.

http://www.masimo.com/rad-57/; Noninvasive Measurement of Methemoglobin, Carboxyhemoglobin and Oxyhemoglobin in the blood. Printed on Aug. 20, 2009.

http://amivital.ugr.es/blog/?tag+spo2; Monitorizacion de la hemoglobina . . . y mucho mas, printed on Aug. 20, 2009.

http://www.masimo.com/spco/; Carboxyhemoglobin Noninvasive > Continuous > Immediate, printed on Aug. 20, 2009.

(56) References Cited

OTHER PUBLICATIONS http://www.masimo.com/PARTNERS/WELCHALLYN.htm; Welch Allyn Expands Patient Monitor Capabilities with Masimo Pulse Oximetry Technology, printed on Aug. 20, 2009.

http://www.masimo.com/pulseOximeter/PPO.htm; Masimo Personal Pulse Oximeter, printed on Aug. 20, 2009.

http://www.masimo.com/generalFloor/system.htm; Masimo Patient SafetyNet System at a Glance, printed on Aug. 20, 2009.

http://www.masimo.com/partners/GRASEBY.htm; Graseby Medical Limited, printed on Aug. 20, 2009.

European Office Action issued in application No. 10763901.5 on Jan. 11, 2013.

Hall, et al., Jeffrey W.; Near-Infrared Spectrophotometry: A New Dimension in Clinical Chemistry; vol. 38; No. 9; 1992.

Kanukurthy et al., "Data Acquisition Unit for an Implantable Multi-Channel Optical Glucose Sensor", Electro/Information Technology Conference, Chicago, IL, USA, May 17-20, 2007, pp. 1-6.

Smith, "The Pursuit of Noninvasive Glucose: 'Hunting the Deceitful Turkey'", 2006.

Small et al., "Data Handling Issues for Near-Infrared Glucose Measurements", http://www.ieee.org/organizations/pubs/newsletters/leos/apr98/datahandling.htm, accessed Nov. 27, 2007.

Japanese Office Action, re JP Application No. 2011-516895, mailed Sep. 2, 2014, with translation.

Office Action for Corresponding European Application No. 10 763 901.5-1660, dated Aug. 6, 2015, in 4 pages.

\* cited by examiner

EMITTER DRIVER FOR NONINVASIVE PATIENT MONITOR

REFERENCE TO RELATED APPLICATIONS

The present application is a continuation of U.S. patent application Ser. No. 12/875,062, filed Sep. 2, 2010, entitled "Emitter Driver for Noninvasive Patient Monitor," which claims priority benefit under 35 U.S.C. §119 (e) from U.S. Provisional Application No. 61/239,741, filed Sep. 3, 2009, entitled "Emitter Driver for Noninvasive Patient Monitor;" the disclosures of which are incorporated herein by reference.

The present disclosure is also related to the following applications.

| App. No. | Filing Date | Title |
| --- | --- | --- |
| 12/534,827 | Aug. 3, 2009 | Multi-Stream Data Collection System for Noninvasive Measurement of Blood Constituents |
| 12/534,812 | Aug. 3, 2009 | Multi-Stream Sensor Front Ends for Noninvasive Measurement of Blood Constituents |
| 12/534,823 | Aug. 3, 2009 | Multi-Stream Sensor for Noninvasive Measurement of Blood Constituents |
| 12/534,825 | Aug. 3, 2009 | Multi-Stream Emitter for Noninvasive Measurement of Blood Constituents |
| 12/497,528 | Jul. 2, 2009 | Noise Shielding for a Noninvasive Device |
| 12/497,523 | Jul. 2, 2009 | Contoured Protrusion for Improving Spectroscopic Measurement of Blood Constituents |
| 29/323,409 | Aug. 25, 2008 | Patient Monitoring Sensor |
| 29/323,408 | Aug. 25, 2008 | Patient Monitor |
| 12/497,506 | Jul. 2, 2009 | Heat Sink for Noninvasive Medical Sensor |

Each of the foregoing is incorporated by reference herein in its entirety.

BACKGROUND OF THE INVENTION

1. Field of the Invention

The present disclosure generally relates to patient monitoring devices and more specifically, embodiments of the present disclosure relate to driving light sources of patient monitoring devices to properly irradiate tissue under observation.

2. Description of the Related Art

Spectroscopic patient monitoring systems including noninvasive patient monitoring systems often energize a plurality of emission devices that irradiate tissue under observation. In many systems, the emission devices irradiate the tissue at different wavelengths at different times. The radiation is scattered and absorbed by the tissue such that some attenuated amount thereof emerges and is generally detected through one or more photodetectors. The photodetectors output one or more signals indicative of the intensity of the detected attenuated radiation and forward the signal to a patient monitor for processing.

In many systems, the patient monitor provides a drive signal configured to activate each emission device at a different time over an activation cycle, thereby reducing a likelihood that a detector seeking a measure of attenuation in light of one wavelength will be effected by radiation from light of another wavelength.

For example, FIG. 1 illustrates a patient monitoring system 100 including a patient monitor 102 communicating with a noninvasive optical sensor 104 through cable 106. As shown in FIG. 1, the monitor 102 displays calculated measurements derived at least in part from processing an output signal from the sensor 104 indicative of light attenuated by pulsing blood. As shown in FIG. 1, the monitor 102 includes a driving circuit 108 configured to drive a sensor light source 110, such as, for example, a two emitter light source configured to emit light at different wavelengths. The emitters shown in FIG. 1 are connected in parallel in a back-to-back configuration, although other configurations and their drive circuitry requirements will be recognizable to an artisan from the disclosure herein, including, for example, common anode, common cathode and the like.

In general, a processor of said monitor 102 controls various latching mechanisms to activate one of voltage-to-current converters 112, 114 at a time. Once activated, the converters 112, 114 provide a current through conductors of the cable 106 to an associated LED 116, 118 of the sensor 104. Thus, the processor may output appropriate latching signals to the driving circuit 108 to precisely control a duty cycle and current level for each of the LEDs 116, 118, and ensure that the LEDs 116, 118 are activated one at a time. Examples of the driver circuitry of FIG. 1 are disclosed in U.S. Pat. No. 6,157,850. The '850 patent disclosure is incorporated in its entirety by reference herein.

In contrast to the driving circuit 108 and light source 110 of FIG. 1, FIG. 2 illustrates a patient monitoring system 200 including a patient monitor 202 communicating with a noninvasive optical sensor 204 through a cable 206. As shown in FIG. 2, the monitor 202 displays calculated measurements derived at least in part from processing an output signal from the sensor 204 indicative of light attenuated by pulsing blood. As shown in FIG. 2, the monitor 202 includes a driving circuit 208 configured to drive a sensor light source 210, such as, a grid array of LEDs capable of emitting light at different wavelengths of radiation.

In general, the driving circuit 208 includes a plurality of row drivers 220 and a plurality of column drivers 222, the activation of a particular row driver and a particular column driver corresponds to the activation of one or a group of LEDs arranged at a corresponding node in a grid of rows 224 and columns 226. Such activation is controlled through one or more processors of said monitor 202 in order to precisely control a duty cycle for each of the LEDs in the grid array, including LEDs 216, 218. For example, row and column drivers 220, 222 function together as switches to Vcc and current sinks, respectively, to activate LEDs and function as switches to ground and Vcc, respectively, to deactivate LEDs. This push-pull drive configuration advantageously prevents parasitic current flow, and thus, parasitic activation, in deactivated LEDs. In a particular embodiment, one row drive line 224 is switched to Vcc at a time. Examples of the driver circuitry of FIG. 2 are disclosed in U.S. pat. app. Pub. No.

2006/0241363. The '363 patent application's disclosure is incorporated by reference in its entirety herein.

SUMMARY OF THE INVENTION

The foregoing LED driver circuits 108, 208 include some limitations. The driver circuit 108 uses a separate drive conductor for each LED of the light source 110. Thus, in the system 100 of FIG. 1, the cable 106 carries N drive currents over N conductors to drive N LEDs. As will be recognizable to an artisan from the disclosure herein, increasing a number LEDs in the light source 110 to, for example, increase a number of available wavelengths, corresponds to increasing a number of conductors in the cable 106. Each increase of conductors carrying high emitter driver currents in the cable increases a likelihood of interference with other conductors of cable 106, such as those conductors communicating sensitive very low currents or voltages at high impedance as output signals from the detectors of the sensor 104. Moreover, each increase of conductors increases cable size, cost, complexity, shielding, cable stiffness, and the like, thereby decreasing patient comfort.

Driver circuit 208, including the row and column drivers 220, 222, is an improvement to the N-to-N driver circuit 108 of FIG. 1. For example, in the system 200 of FIG. 2, the cable 206 carries N high emitter driver currents on N conductors. Half of the N conductors correspond to high current row drive signals and half correspond to high current column drive signals. These N conductors allow a processor to address and thus activate specific nodes of a light source grid array of 2*N nodes. Similar to the N-to-N driver circuit 108, an artisan will recognize from the disclosure herein, that increasing a number LEDs in the light source grid array 210 to, for example, increase a number of available wavelengths, corresponds to increasing a number of conductors in the cable 206, thereby potentially increasing a likelihood of harmful interference in detector signals.

Based on at least the foregoing, when a need exists to increase a number of different wavelength LEDs to accommodate more sophisticated signal processing of patient monitors, a need exists to find better solutions for driving light sources. Often, increasing available wavelengths corresponds to seeking to measure physiological parameters that are more difficult to distinguish from surrounding noise, including, for example, total hemoglobin monitors, glucose monitors, methemoglobin monitors, combinations of the same or the like, or corresponds to increasing the sensitivity in conventional pulse oximeters. However, simply increasing a number of high current conductors in a given cable 106, 206 can be fraught with drawbacks including cable stiffness and crosstalk noise on detector conductors.

Accordingly, embodiments of the present disclosure include a patient monitoring system where a patient monitor employs addressing schemes to increase a number of specifically selectable activation nodes of a light source. In an embodiment, an emitter driver is configured to address substantially $2^N$ nodes, where N is a number cable conductors configured to carry activation instructions from a processor. In an embodiment, an address controller outputs an activation instruction to a latch decoder configured to supply switch controls to logic devices governing the activations of LEDs of a light source. In an embodiment, N cable conductors can be used to uniquely address all or substantially all of $2^N$ LED nodes. In certain embodiments, the activation instruction need not be a high current signal. For example, in some of the presently disclosed embodiments, a cable carries one or a few high current emitter driver signals, which can be routed through logic and addressing to a desired node of the light source. For example, in an embodiment where each LED of a light source can be driven with the same or similar current, embodiments of the cable of the present disclosure may carry a single high current conductor. In embodiments where LEDs of a light source may use different currents to drive different types of LEDs, such as, for example, light sources including superluminescent, laser or side emitting LEDs, along with more traditional LEDs, embodiments of the cable of the present disclosure may carry currents appropriate for each type of LED over a plurality of high current conductors. In many embodiments, however, the number of high current conductors is dramatically reduced from that of the drivers disclosed in the Background herein.

Embodiments of the present disclosure include a non-invasive physiological sensor configured to output one or more signals indicative of one or more physiological conditions of a patient being monitored. The sensor includes a plurality of light emitting sources configured for transmitting optical radiation to a measurement site. The sensor also includes one or more detectors configured to output said one or more signals responsive to said optical radiation detected after attenuation by body tissue of said patient at said measurement site. The one or more signals are indicative of said one or more physiological conditions of said patient. The sensor also includes a plurality of switches configured for selectively connecting one or more of the light emitting sources to one or more drive signals. Additionally, the sensor includes a decoder circuit configured for controlling the plurality of switches, wherein when said decoder circuit receives N inputs, said decoder circuit configured to selectively address up to $2^N$ unique locations. Each location includes one or more of said plurality of said semiconductor switches, wherein activation of one of said unique locations causes at least one of said light emitting sources to transmit said optical radiation to said measurement site.

Embodiments of the disclosure also include a cable communicating signals between a patient monitor and a noninvasive optical sensor. The cable comprises one or more signal lines configured to carry one or more drive signals configured to activate one or more light sources of said noninvasive optical sensor. The cable also includes N address lines capable of selecting $2^N$ unique locations and configured to selectively connect up to about $2^N$ light emitting sources to ones of said one or more drive signals. The connection activating said light emitting sources to provide light to tissue of a patient wearing said sensor and allowing one or more photodetectors to detect light from said activated sources after attenuation by tissue from said patient.

In still other embodiments, the disclosure includes a method to selectively drive light emitting sources in a noninvasive optical physiological sensor for monitoring parameters of a patient. The method includes attaching said sensor to a patient where said sensor includes at least one different semiconductor switch in series with each of the light emitting sources. The method also including activating said semiconductor switches to connect associated light emitting sources to a drive signal. The light emitting source transmits optical radiation into a measurement site of said patient, and said activation comprises providing N conductors to a decoder capable of controlling about $2^N$ of the semiconductor switches and configured to control up to about $2^N$ of the semiconductor switches.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

The following drawings and the associated descriptions are provided to illustrate embodiments of the present disclosure and do not limit the scope of the claims.

FIG. 7A illustrates a first method of shorting unused LEDs and FIG. 7B illustrates a second method of shorting unused LEDs.

DETAILED DESCRIPTION OF THE PREFERRED EMBODIMENT

Embodiments of the present disclosure include a patient monitoring system including a patient monitor having a driving circuit advantageously capable of selectively activating $2^N$ LEDs of a light source using a decoder receiving an N signal address. In various disclosed embodiments, use of addressing and a decoder advantageously reduces a number of high current conductors in a cable communicating signals between the monitor and, for example, a noninvasive sensor. For example, in embodiments where a light source includes LEDs configured to be driven by a single current, embodiments of the present disclosure provide that the cable may carry a single high current conductor. In other embodiments where the light source includes LEDs configured to be driven at a first current and additional LEDs configured to be driven at a second current different from the first, embodiments of the present disclosure provide that the cable may carry the plurality of high current conductors, one for each current required. While some embodiments shown herein require two currents, an artisan will recognize from the disclosure herein how to add additional currents when LED configurations so require.

In the foregoing embodiments, the driver circuit advantageously includes use of addressing and a decoder, the addressing information carried over conductors carrying lower, less interfering signals than those of driving currents. Accordingly, embodiments of the present disclosure reduce the potential of harmful crosstalk between high current conductors carrying driver signals and low current conductors carrying, for example, sensitive detector signals. Moreover, cables associated with the present disclosure may advantageously require fewer larger heavily shielded driver conductors, and therefore, may be less costly to produce, be less rigid or stiff and thus more ergonomic to a wearer of a sensor.

In additional embodiments, each LED is shorted by a transistor that is conducting unless that particular LED is activated. Such shorting advantageously reduces the likelihood of unwanted emissions by LEDs emitting unwanted wavelengths due to, for example, parasitic currents. Also, various embodiments include on/off timing hardware configured to govern the shorting transistors to improve timing of LED activations and deactivations.

To facilitate a complete understanding of the invention, the remainder of the detailed description references to the drawings, wherein like reference numbers are referenced with like numerals throughout.

Figure 1:
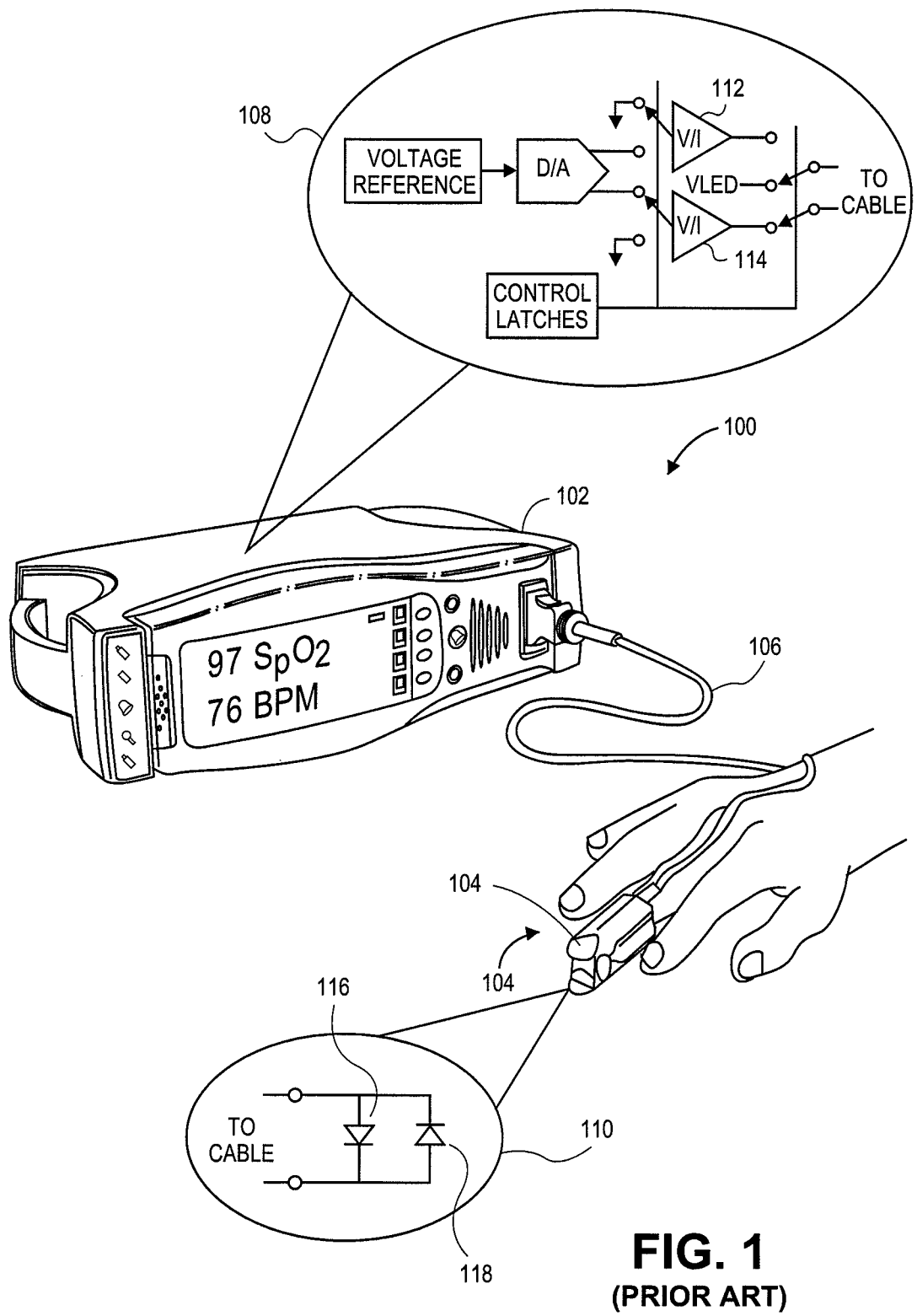
FIG. 1 illustrates a traditional patient monitoring system including a patient monitor communicating with a noninvasive optical sensor through a cable.
Figure 2:
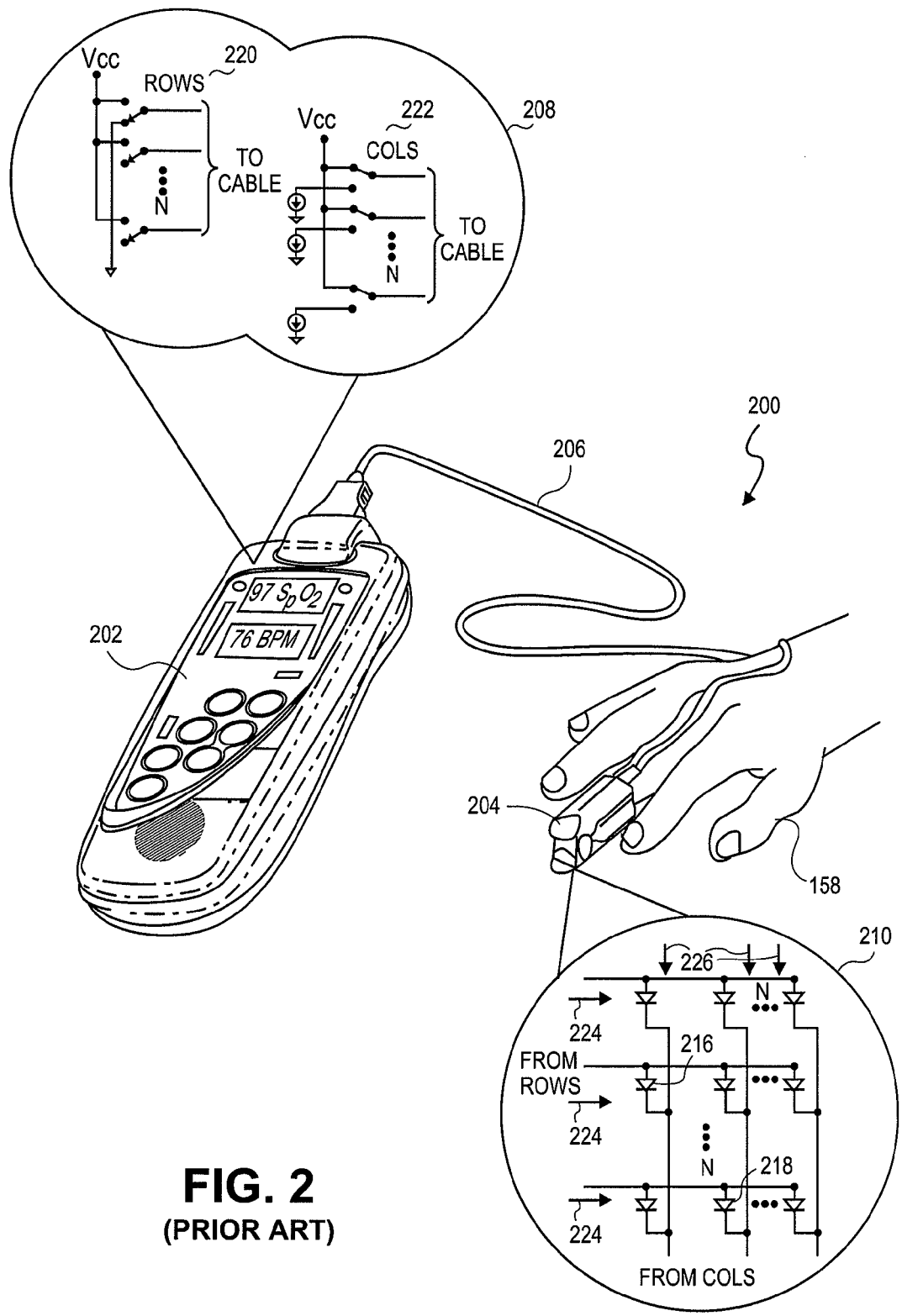
FIG. 2 illustrates another traditional patient monitoring system including a patient monitor communicating with a noninvasive optical sensor through a cable.
Figure 3:
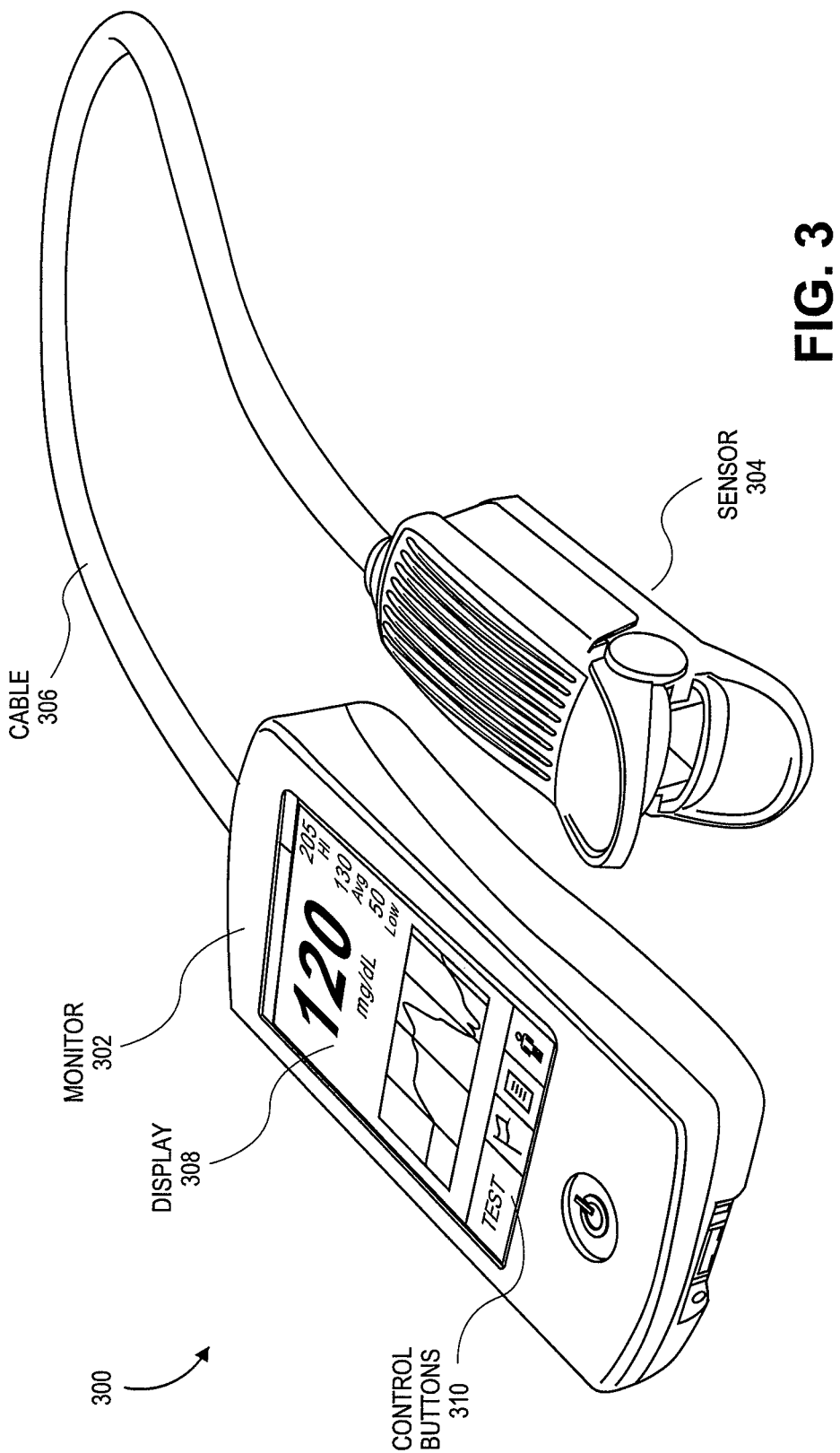
FIG. 3 illustrates a patient monitoring system according to embodiments of the present disclosure.

FIG. 3 illustrates a patient monitoring system 300 according to embodiments of the present disclosure. As shown in FIG. 3, the system 300 includes a patient monitor 302, a noninvasive sensor 304 communicating with the monitor 302 through a cable 306. The monitor 302 drives a lights source including a plurality of emitters of the sensor 304 to irradiate tissue of a wearer of the sensor 304. The sensor 304 also includes one or more photodetectors that detect light attenuated by the body tissue and output one or more signals indicative of the detected light. The monitor 302 receives the one or more output signals of the sensor 304, processes the signals and determines one or more measurement values of various physiological characteristics of the wearer. The monitor 302 includes a display 308 configured to provide alphanumeric and/or graphical information to a caregiver. The monitor 3021 also includes a plurality of user input devices 310 including for example, a touch screen and one or more input keys. An artisan will recognize from the disclosure herein that the input devices 310 could comprise one or a combination of control buttons, dials, knobs, or the like, touch screen inputs, vocal commands, or the like.

Although disclosed as a portable handheld device, an artisan will recognize from the disclosure herein that the monitor 302 may comprise a desktop or stationary monitor, may monitor some or many parameters, may output information to legacy caregiver systems, may wirelessly communicated between sensors and monitors, between monitors and other monitors, combinations of the same and the like.

Figure 4:
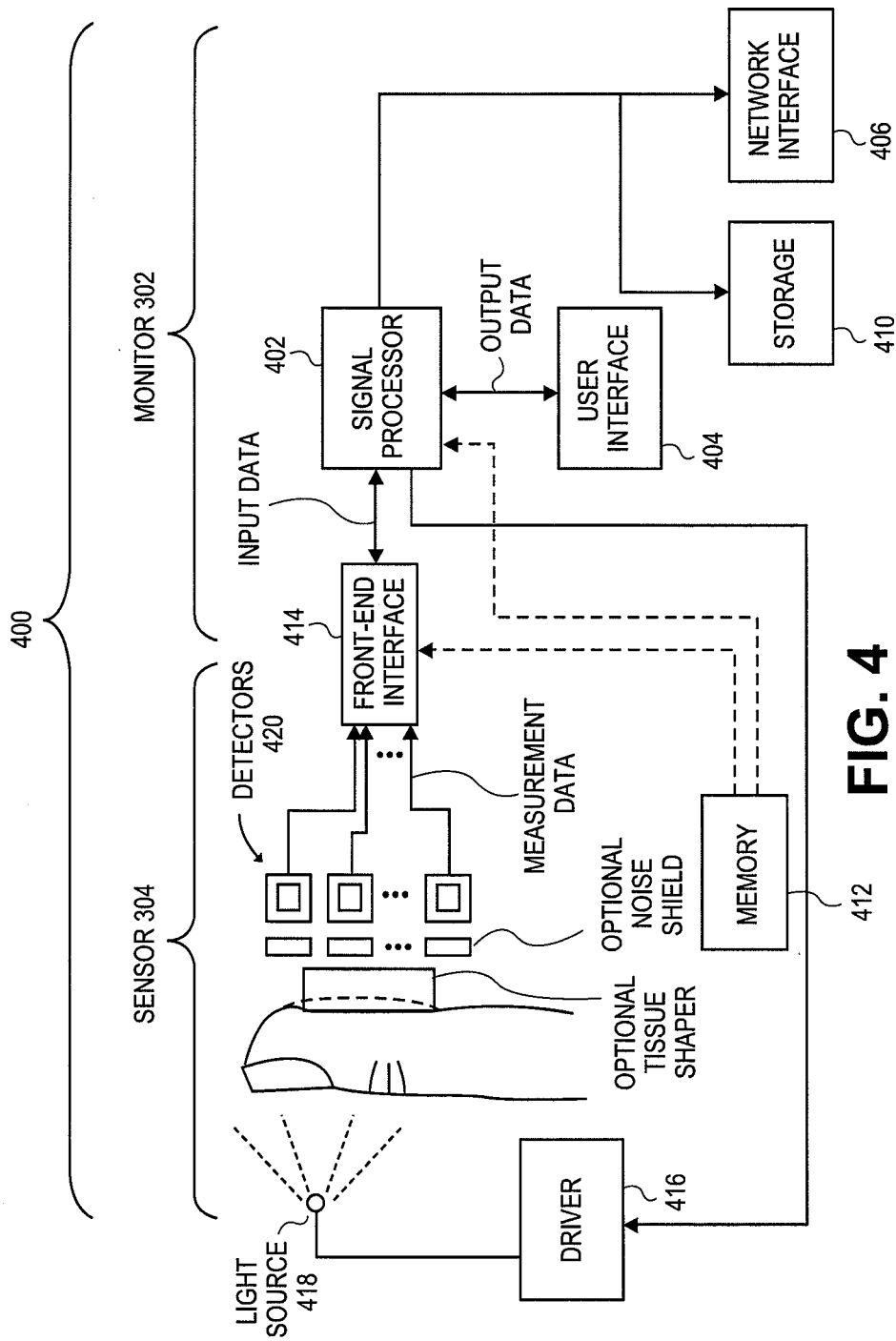
FIG. 4 illustrates an exemplary block diagram of embodiments of the system of FIG. 3.

FIG. 4 illustrates an exemplary block diagram 400 of embodiments of the monitor 302 of the system of FIG. 3. As shown in FIG. 4, the monitor 302 may include one or more signal processors 402 communicating with a user interface 404, network interface 406, memory and storage 410, sensor and/or cable memory 412, a front end interface 414 and driver circuitry 416. In general, the processor 402 outputs control data to the driver circuitry 416, which in turn selectively activates LEDs of a light source 418 to irradiate tissue, such as, for example a digit of the wearer. The tissue absorbs the irradiation and one or more detectors 420 detect the attenuated light. The detectors output one or more signals indicative of the attenuated light to the front end interface 414, which filters and pre-process the output signal. Signal processor 402 receives the processed and filtered output signal and determines measurement values for the one or more monitored parameters.

In various embodiments, the sensor 304 may include a tissue shaper configured to mechanically stabilize and/or control the shape of the digit at the measurement site. In an embodiment, the tissue shaper may advantageously include a bump including a substantially cylindrical surface. Additional embodiments of the tissue shaper are disclosed in U.S. patent application Ser. No. 12/534,827, filed on Aug. 3, 2009.

The teachings of the '827 application relating to the tissue shaper are incorporated by reference in its entirety herein. Additionally, advantages are found in the spatial arrangement of the detectors, the number of detectors 420 and in noise shielding structures of the sensor 304. Disclosures pertaining thereto can also be found in the '827 application, and those disclosures are also incorporated by reference in their entirety herein.

In addition to the foregoing, the processor 402 is also configured to execute measurement determination software instructions that use received detector signal data preprocessed by the front end 414 to determine output measurement values for one or more parameters of the tissue. Exemplary algorithms for determining measurement values can be found in U.S. Pat. No. 6,157,850, U.S. patent application Ser. No. 12/534,827, filed on Aug. 3, 2009 and Ser. No. 11/366,209, filed on Mar. 1, 2006. The disclosure relating to determination of measurements from input sensor data is incorporated from each of the foregoing documents in its entirety by reference herein.

Figure 5:
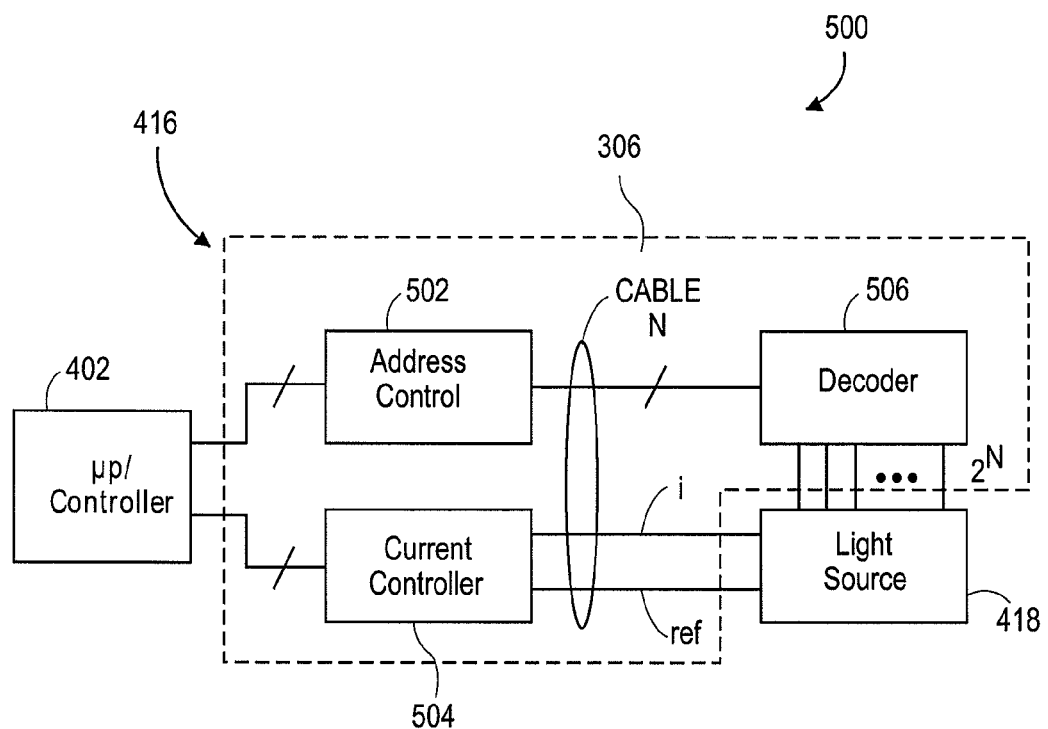
FIG. 5 illustrates an exemplary block diagram of embodiments of a driver of FIG. 4.

FIG. 5 illustrates an exemplary block diagram 500 of embodiments of the driver 416 of FIG. 4. As shown in FIG. 5, the processor 402 communicates with an address control 502 and one or more driving current controllers 504 to precisely control activation of the light source 418. In an embodiment, the address control 502 outputs an address, such as, for example, a binary number, to a decoder 506. The decoder 506 decodes the address and identifies particular LED(s) of the light source 418 to be connected to the current source 504. Once connected, current flows through the particular LED, thereby activating it to irradiate tissue. In an embodiment, the decoder comprises an N-to-$2^N$ decoder, which an artisan will recognize from the disclosure herein to include its broad ordinary meaning, including a decoder that accepts an address word, such as, for example, a binary set of N bits, and associates that word with a particular LED node. For example, a 4 bit word uniquely identifies 16 possible LEDs. However, extension of just an additional 4 bits to an 8 bit word uniquely identifies up to 256 possible LEDs or LED locations. Examples of the decoder 506 are commercially available from vendors such as Fairchild Semiconductor, Texas Instruments, NXP Semiconductors, or the like.

In an embodiment, the current controller 504 may comprise logic allowing the processor 402 the ability to select from a plurality of differing currents levels. For example, when the light source 418 comprises, for example, LED devices and more powerful superluminescent, laser or side emitting LEDs, the driver 416 adjusts the current controller 504 to provide the appropriate current to the appropriate LED at the appropriate address. For example, the current controller 504 may advantageously select an appropriate one of a plurality of currents depending on a type of LED addressed by the processor 402 through the address decoder 506.

In an embodiment, the current controller 504 seeks to keep current patterns similar regardless of whether LEDs are activated or not. In embodiments having a plurality of different currents, twisting the conductors on which the currents travel in opposite direction to the input data wires in the cable 306 has been shown to reduce effects of crosstalk on other conductors in the cable 306.

FIG. 5 also shows that the address control 502 and current controller 504 may advantageously be housed in the monitor 302, although an artisan will recognize from the disclosure herein that one or more of the controls 502, 504 could reside anywhere along the path from the monitor 302 to the sensor 304, including the various connectors of the monitor 302, the cable 306 and the sensor 304. As shown in FIG. 5, the cable 306 includes conductors for the N address lines, the current sources, ground, shield, and other needs, such as, for example, conductors communicating with a thermister, one or more memories, or other desired sensor devices.

Figure 6:
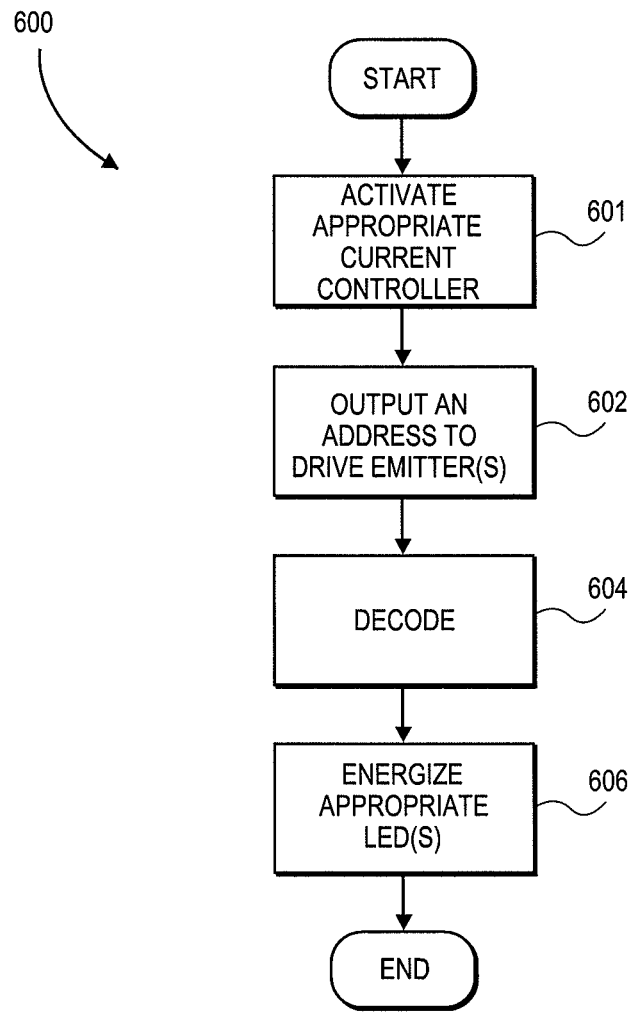
FIG. 6 illustrates an exemplary flowchart of a driving process according to embodiments of the present disclosure.

FIG. 6 illustrates an exemplary flowchart of a driving process 600 according to embodiment of the present disclosure. In block 601, the processor 402 activates the current controller to output an appropriate current. In an embodiment of multiple current sources, the activation includes a selection of an appropriate current, as will be discussed further with respect to FIGS. 8 and 9. In block 602, the processor 402 outputs an address of a particular LED to be activated. In block 604, the N-to-$2^N$ decoder 506 receives the address and determines the unique output to be activated. In an embodiment, the determination includes translation of a binary or other word to activation of logic transistors configured to connect a particular LED to the current source and in some embodiments, disconnect a short around the same LED. In block 606, the decoder 506 activates the appropriate logic devices to connect the appropriate LED to the appropriate current controller 504 for the duration of the determined duty cycle. In an embodiment, the address control 502 comprises latches set by the processor 402 in order to control for each LED the on and off timing. In an embodiment, one node is energized at a time, and in further embodiments, some time spacing or gap is provided between consecutive activations to guard against interference at the detector by light of differing wavelengths. In an embodiment, the gap, or no LED activation occurs between activations of LEDs. In an embodiment, the gap comprises one of the $2^N$ addressable locations such that an all-off condition is specifically addressable by the processor 402. In an embodiment, the addressable all-off condition may comprise multiple addresses, one for each current level available from the current controller 504.

Although disclosed with reference to process 600, an artisan will recognize from the disclosure herein that other processes may be used to selectively address an activation location or group of activation locations of a light source and supply the location or group of activation locations with the appropriate amount of current.

Figure 7A:
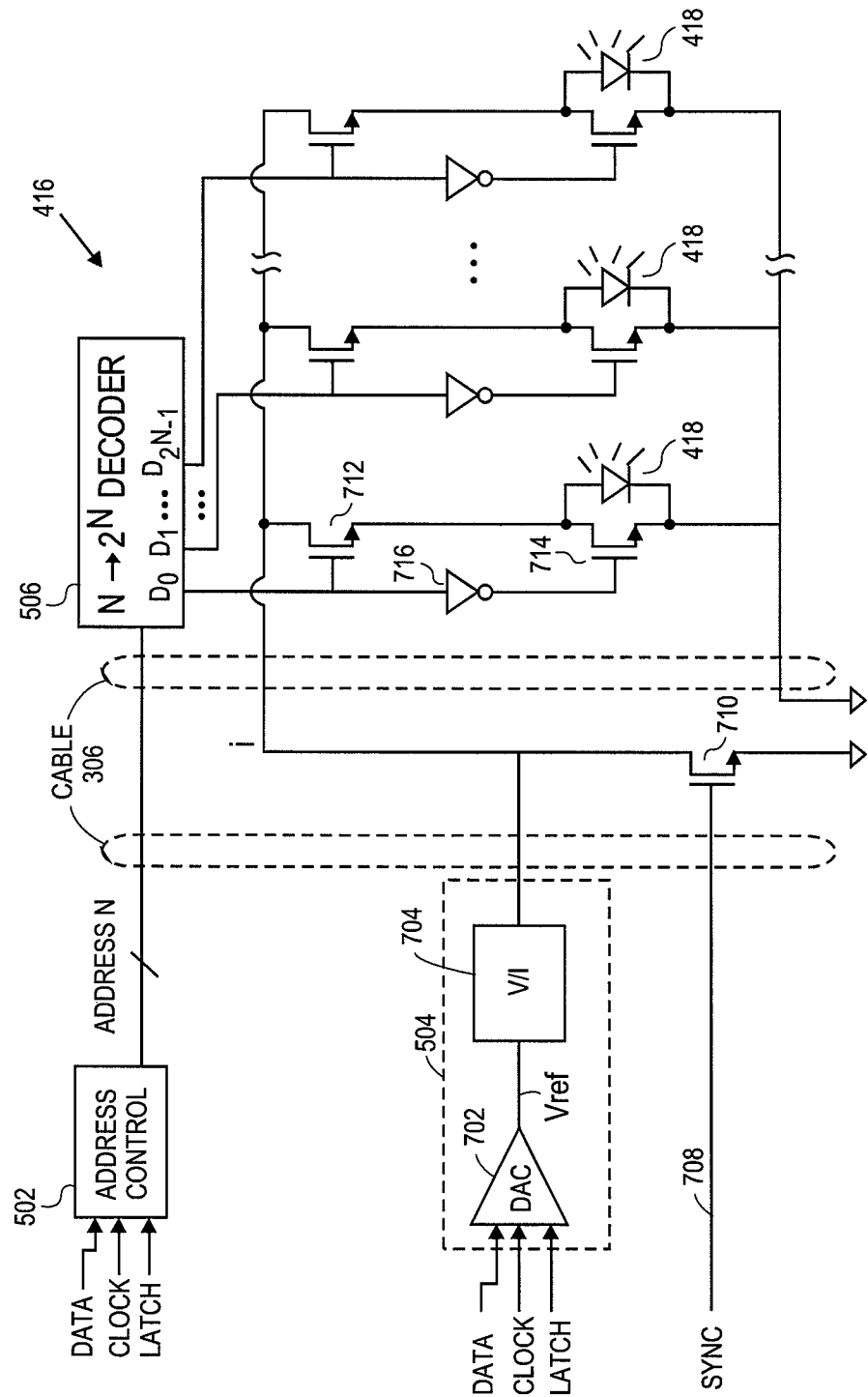
FIGS. 7A-7B illustrates exemplary block diagrams of alternative embodiments of the driver of FIG. 4, where
Figure 7B:
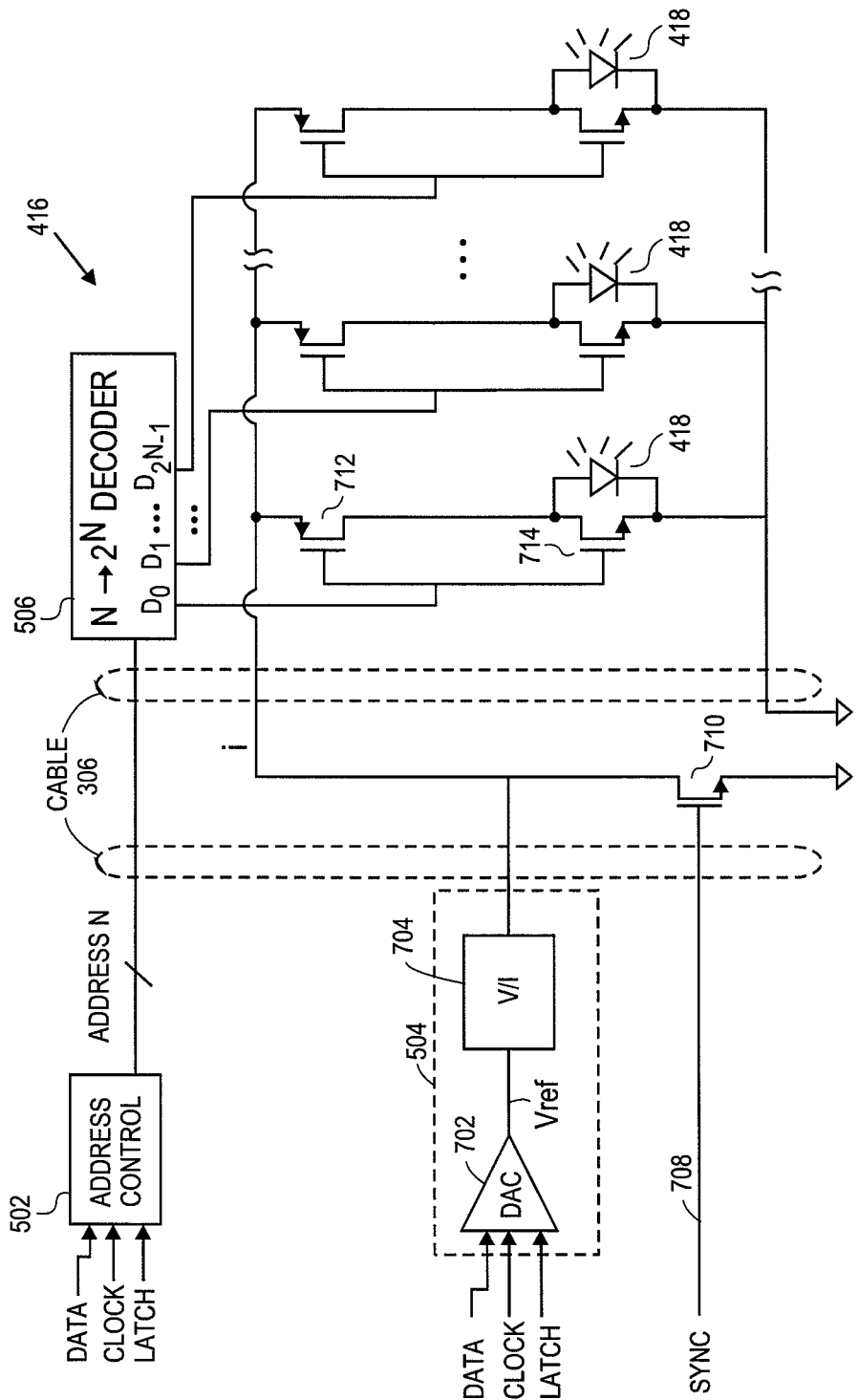

FIGS. 7A and 7B illustrate exemplary block diagrams of embodiments of the driver 416 driving the light source 418 of FIG. 4, where the driver 416 includes a single current controller. As shown in FIGS. 7A and 7B, the driver 416 includes the address control 502, the current controller 504, and the decoder 506. In an embodiment, the current controller 504 includes a converter 702 converting digital signals from the processor into analog output. In an embodiment, the DAC 702 controls light saturation by allowing for the fine tuning of the output drive current. The DAC 702 receives clock and data signals from the processor and a latching signal dictating when the DAC should lock the data on the data signal and stabilize the output drive current.

The output of the DAC 702 is provided to amplifier 704 which in an embodiment includes a precision voltage-to-current amplifier that adjusts its output current based on the input voltage. The output of the amplifier 704 is also provided as the driving current to the LEDs of the light source 418, in an embodiment, through the cable 306. A SYNC signal 708 is provided to ensure precision on/off timing to the LED addressed by the decoder 506. Imperfections in the circuitry and parasitic parameters may cause the rise and fall times for the current i to be less precise than desired. The SYNC signal 708 can advantageously be timed to sink to ground some or all of the imperfections and parasitic parameters that occur during rising or falling current through the LED 418 through a logic switching device 710. Sinking these imperfections advantageously produces a higher quality current, which produces better on/off activation of the light source 418, which provides for a better signal to noise ratio. In an embodiment, the sync signal 708 is combined to create a single output current i. In an embodiment, the output current may comprise about 0-about 80 mA, controlled at least in part by the voltage provided by the processor 402 to the DAC 702.

As shown in FIGS. 7A and 7B, control logic ensures that each LED of the light source 418 can activate only when its location is decoded by the decoder 506. For example, when a particular location is inactive, a first logic device 712 is biased open such that current cannot flow through it. A second logic device 714 is biased closed to create a short around the LED at the inactive location; the short is also connected to ground. Thus, were any parasitic current to appear on the drive conductor for the particular location, it will be simply shorted to ground and cannot cause the LED to emit radiation. When the decoder 506 receives the address of the particular location, the first logic device 712 is biased closed and the second logic device 714 is biased open. The closing of device 712 connects the second logic device and the LED of the particular location to the current i of the current controller 504. The opening of device 714 removes the short around the LED, which is now connected to the drive current i, and the LED activates to emit light at its designated wavelength.

In the embodiment shown in FIG. 7A, an inverter 716 is placed at one the gates of the logic devices 712 and 714, causing them to oppose one another. For example, a single control signal from the decoder 504 is supplied to the gate of device 712 causing it to open or close, and its opposite is supplied to the gate of device 714 causing it to respectively close or open. In the embodiment shown in FIG. 7B, devices 712 and 714 are opposite devices such that a same signal from the decoder 504 applied to both gates causes one of the devices 712 to open and close while the other 714 respectively closes and opens.

An artisan will recognize from the disclosure herein other logic devices and schemes to assist in precisely governing the on/off cycles of each LED of the light source 418 while simultaneously precisely governing the drive current to the same.

As can also be seen in FIGS. 7A and 7B, the cable 306 carries conductors for the output of the current controller 504 and the address control. In alternative embodiments, the cable 306 may also carry the SYNC signal. Thus, in various embodiments, the cable 306 may advantageously include a single high current signal, N address signals and still be able to uniquely activate substantially $2^N$ light source nodes. In an embodiment, "substantially" may be defined to be when one or more of the $2^N$ light source nodes correspond to a null set where no nodes are active. The null set is advantageous to ensure spacing between LED activations.

Figure 8:
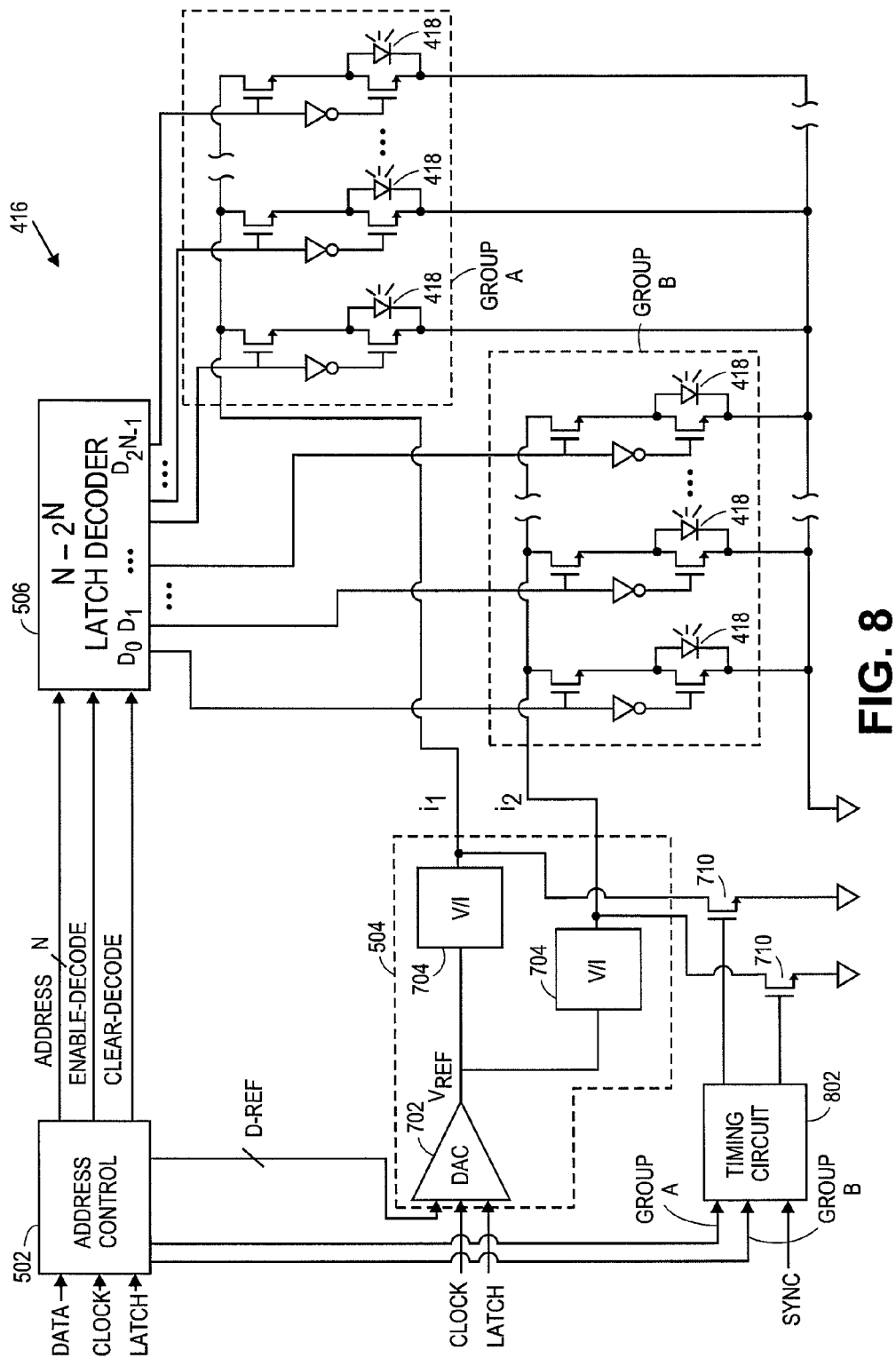
FIG. 8 illustrates another exemplary block diagram of an embodiment of the driver of FIG. 4 configured to drive LEDs with different drive current requirements.

FIG. 8 illustrates another exemplary block diagram of embodiments of the driver 416 driving the light source 418 of FIG. 4, where the driver 416 comprises a plurality of current controllers 504. As shown in FIG. 8, the current controller 504 outputs two different currents $i_1$ and $i_2$ set by the voltage output by the converter 702 governed by the processor 402. FIG. 8 further shows output current $i_1$ communicating with the nodes of a first group of LEDs, Group A, and the output current $i_2$ communicating with the nodes of a second group of LEDs, Group B. In an embodiment, $i_1$ may comprise about 0-about 80 mA, while $i_2$ may comprise about 0-about 800 mA. An artisan will recognize that other embodiments may advantageously employ other currents and/or have more or less groups.

Thus, in an embodiment where some of the LEDs of the light source 418 comprise LEDs driven at greater power; those LEDs may advantageously communicate with the output of the current source $i_2$. Also shown in FIG. 8 is timing circuit 802 including logic configured to provide appropriate SYNC signals to logic devices 710 for sinking each of currents $i_1$ and $i_2$ similar to that disclosed with reference to FIGS. 7A and 7B.

In an embodiment, the amplifier 704 comprises a plurality of amplifiers and resistors in a feedback configuration to provide a stabilized current based on an input voltage. Such configurations are known to an artisan from the disclosure herein. In an embodiment, the timing circuit 802 comprises logic combinations of signals to ensure only one of the currents $i_1$ and $i_2$ can flow to ground at a time. In an embodiment, the SYNC signal is logic ANDed with each of the Group A, Group B signals such that the SYNC and Group A signals must match to open a first logic switch device 710 and allow current $i_1$ to flow, and SYNC and Group B signals must match to open a second logic switch device 710 and allow current $i_2$ to flow.

Figure 9:
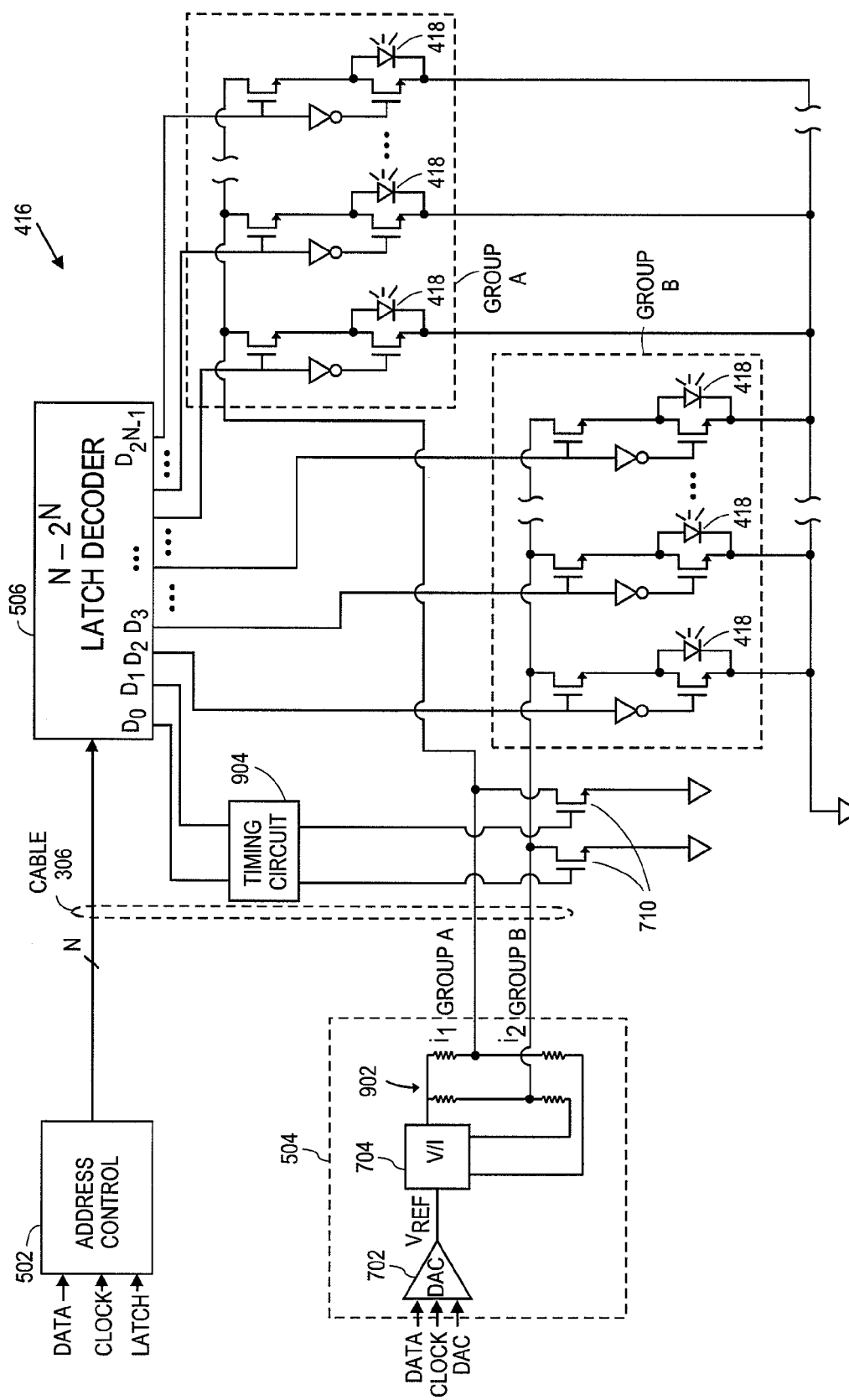
FIG. 9 illustrates another exemplary block diagram of an embodiment of the driver of FIG. 4 configured to drive LEDs while avoiding a SYNC signal through a patient cable.

FIG. 9 illustrates another exemplary block diagram of embodiments of the driver 416 driving the light source 418 of FIG. 4, where the driver 416 comprises a plurality of current controllers 504. However, in FIG. 9, the current controller 504 outputs two different currents $i_1$ and $i_2$ using a single amplifier 704 and analog circuitry 902 that produces the currents $i_1$ and $i_2$ for Group A and Group B LEDs. Moreover, FIG. 9 illustrates the SYNC signal functionality and the signal itself as part of the sensor 104. For example, in this embodiment, two locations or addresses available on the decoder 505 correspond to the SYNC signals of FIG. 8, such that the processor 402 produces the SYNC signals not as processor outputs, but as addresses of the controller 504. Timing circuit 904 includes logic to ensure only one of the currents $i_1$ and $i_2$ can flow to ground at a time by controlling logic device 710 now on the sensor 304. Thus, in the embodiment of FIG. 9, the processor 402 advantageously replaces output signals with addressing. The advantages of this embodiment include the sinking of parasitic currents and imperfections on the LED driver 416 itself, and particularly on the sensor 304, which is downstream from the cable 306. In some cases, the cable 306 produces many of the parasitic currents and imperfections due to resistance, inductance and capacitance (or the like) associated with the conductors and conductive materials of the cable 306. Sinking these harmful effects downstream on the sensor ensures that they do not effect the operation of the LEDs 418.

Although the driver circuitry is disclosed with reference to its preferred and alternative embodiments, the disclosure is not intended to be limited thereby. Rather, a skilled artisan will recognize from the disclosure herein a wide number of alternatives for driver, including, for example, employing an amplifier/DAC for each group of current controllers to increase performance thereof. Also, the artisan will recognize from the disclosure herein that the address control, the decoder, and the current controllers can individually be placed anywhere along the monitoring path. For example, the components can be housed in the monitor 302, in the sensor 304, or in the cable 306 or connectors associated with any of the foregoing.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

Moreover, all publications, patents, and patent applications mentioned in this specification are herein incorporated by reference to the same extent as if each individual publication, patent, or patent application was specifically and individually indicated to be incorporated by reference.

What is claimed is:

1. A cable configured to communicate signals between a patient monitor and a noninvasive optical sensor, the cable comprising:
   one or more signal lines configured to carry one or more drive signals to one or more optical radiation sources of the noninvasive optical sensor;
   N address lines configured to carry N address signals, N being greater than 2; and
   a decoder comprising N input terminals and up to $2^N$ output terminals, the decoder configured to receive the N address signals from the N address lines via the N input terminals and to implement an addressing system capable of selectively individually addressing $2^N$ unique outputs based on the N address signals, the decoder configured to activate an output terminal of the up to $2^N$ output terminals based on the N address signals thereby activating the one or more optical radiation sources to provide optical radiation to tissue of the patient wearing the noninvasive optical sensor and allowing one or more photodetectors of the noninvasive optical sensor to detect the optical radiation after attenuation by the tissue.

2. The cable of claim 1, wherein the one or more signal lines comprise at least two signal lines configured to carry first and second drive signals, one of the at least two signal lines configured to carry a different peak current level from the other of the at least two signal lines.

3. The cable of claim 2, wherein the one of the at least two signal lines is configured to electrically connect to a first group of the one or more optical radiation sources, and the other of the at least two signal lines is configured to electrically connect to a second group of the one or more optical radiation sources different from the first group.

4. The cable of claim 1, wherein the one or more signal lines comprise at least two signal lines configured to carry first and second drive signals, and one of the at least two signal lines is configured to electrically connect to a first group of the one or more optical radiation sources and the other of the at least two signal lines is configured to electrically connect to a second group of the one or more optical radiation sources different from the first group.

5. The cable of claim 1, further comprising:
   a first control line configured to carry an enable signal; and
   a second control line configured to carry a clear signal.

6. The cable of claim 1, further comprising:
   an input connector configured to receive the one or more drive signals and the N address signals from the patient monitor;
   an output connector configured to provide the one or more drive signals and an activation signal from the activated output terminal to the noninvasive optical sensor; and
   a flexible conduit connecting the input connector to the output connector.

7. The cable of claim 1, further comprising an output connector configured to connect to the noninvasive optical sensor, the decoder being embedded in the output connector.

8. The cable of claim 1, wherein the up to $2^N$ output terminals comprise $2^N$ output terminals.

9. The cable of claim 1, wherein the N address signals comprise a set of N bits received in parallel.

10. A method of operating a noninvasive optical sensor, the method comprising:
    providing, by one or more signal lines, one or more drive signals to one or more optical radiation sources of the noninvasive optical sensor;
    providing, by N address lines, N address signals to N input terminals of a decoder, the decoder configured to implement an addressing system capable of selectively individually addressing $2^N$ unique outputs based on the N address signals, N being greater than 2; and
    activating an output terminal of up to $2^N$ output terminals of the decoder based on the N address signals causing at least one of the one or more optical radiation sources to transmit optical radiation to tissue of a patient, thereby allowing one or more photodetectors of the noninvasive optical sensor to detect the optical radiation after attenuation by the tissue.

11. The method of claim 10, wherein the one or more drive signals comprise first and second drive signals, the first drive signal having a different peak current level from the second drive signal.

12. The method of claim 11, further comprising providing the first drive signal to a first group of the one or more optical radiation sources electrically connected to one of the one or more signal lines and providing the second drive signal to a second group of the one or more optical radiation sources electrically connected to the other of the one or more signal lines, the second group being different from the first group.

13. The method of claim 10, wherein the one or more drive signals comprise first and second drive signals, and further comprising providing the first drive signal to a first group of the one or more optical radiation sources electrically connected to one of the one or more signal lines and providing the second drive signal to a second group of the one or more optical radiation sources electrically connected to the other of the one or more signal lines, the second group being different from the first group.

14. The method of claim 10, further comprising:
    providing, by a first control line, an enable signal to the decoder; and
    providing, by a second control line, a clear signal to the decoder.

15. The method of claim 10, further comprising:
    receiving, by an input connector, the one or more drive signals and the N address signals from a patient monitor; and
    providing, by an output connector, the one or more drive signals and an activation signal from the activated output terminal to the noninvasive optical sensor.

16. The method of claim 10, wherein the up to $2^N$ output terminals comprise $2^N$ output terminals.

17. The method of claim 10, wherein the N address signals comprise a set of N bits received in parallel.

18. A patient monitor configured to communicate with a noninvasive optical sensor, the patient monitor comprising:
    a processor configured to select a desired wavelength of optical radiation emitted by one or more optical radiation sources of the noninvasive optical sensor;
    a current control circuit configured to supply a current to the one or more optical radiation sources; and
    an address control circuit configured to set a wavelength of the optical radiation emitted by the one or more optical radiation sources to the desired wavelength by outputting an address of $2^N$ addresses as a set of N bits transmitted separately via N output terminals, each of at least some of the $2^N$ addresses uniquely corresponding to a different wavelength of the optical radiation emitted by the one or more optical radiation sources, N being greater than 2.

19. The patient monitor of claim 18, wherein the current control circuit is configured to supply a level of the current depending at least on the output address.

20. The patient monitor of claim 18, further comprising an input configured to receive an output signal from the noninvasive optical sensor in response to the address control circuit outputting the address, the output signal indicative of one or more physiological conditions of a patient being monitored and responsive to the optical radiation with the desired wavelength detected after attenuation by body tissue of the patient at a measurement site.

* * * * *

UNITED STATES PATENT AND TRADEMARK OFFICE
CERTIFICATE OF CORRECTION

| | |
|---|---|
| PATENT NO. | : 9,186,102 B2 |
| APPLICATION NO. | : 14/227230 |
| DATED | : November 17, 2015 |
| INVENTOR(S) | : Johannes Bruinsma |

It is certified that error appears in the above-identified patent and that said Letters Patent is hereby corrected as shown below:

Specification
In column 6 at line 30, Change "3021" to --302--.

Signed and Sealed this
Twenty-fourth Day of May, 2016

Michelle K. Lee
*Director of the United States Patent and Trademark Office*